United States Patent
Miyazaki et al.

(10) Patent No.: US 9,239,282 B2
(45) Date of Patent: Jan. 19, 2016

(54) METAL PIPE CORROSION MONITORING DEVICE AND USE THEREOF

(71) Applicant: NAIGAI CHEMICAL PRODUCTS CO., LTD., Tokyo (JP)

(72) Inventors: Haruhisa Miyazaki, Aichi (JP); Katsumasa Murata, Aichi (JP); Kazuo Marugame, Tokyo (JP); Masaki Yoshida, Tokyo (JP); Yusuke Suetake, Tokyo (JP)

(73) Assignee: NAIGAI CHEMICAL PRODUCTS CO., LTD., Tokyo (JP)

( * ) Notice: Subject to any disclaimer, the term of this patent is extended or adjusted under 35 U.S.C. 154(b) by 85 days.

(21) Appl. No.: 14/355,304

(22) PCT Filed: Oct. 30, 2012

(86) PCT No.: PCT/JP2012/078042
§ 371 (c)(1),
(2) Date: Apr. 30, 2014

(87) PCT Pub. No.: WO2013/065686
PCT Pub. Date: May 10, 2013

(65) Prior Publication Data
US 2014/0306726 A1    Oct. 16, 2014

(30) Foreign Application Priority Data
Nov. 1, 2011 (JP) .................................. 2011-240364

(51) Int. Cl.
| G01R 27/08 | (2006.01) |
|---|---|
| G01N 17/04 | (2006.01) |
| F22B 37/38 | (2006.01) |
| G01N 17/00 | (2006.01) |

(52) U.S. Cl.
CPC ................ *G01N 17/04* (2013.01); *F22B 37/38* (2013.01); *G01N 17/006* (2013.01)

(58) Field of Classification Search
None
See application file for complete search history.

(56) References Cited

U.S. PATENT DOCUMENTS

| 4,283,200 | A | 8/1981 | Bodmer et al. |
|---|---|---|---|
| 4,839,580 | A * | 6/1989 | Moore .................. G01R 27/02 |
| | | | 324/606 |

(Continued)

FOREIGN PATENT DOCUMENTS

| FR | 2417096 | 9/1979 |
|---|---|---|
| JP | 08-028803 | 2/1996 |

(Continued)

OTHER PUBLICATIONS

Search report from E.P.O., mail date is May 12, 2015.

*Primary Examiner* — Minh N Tang
(74) *Attorney, Agent, or Firm* — Greenblum & Bernstein, P.L.C.

(57) ABSTRACT

A metal pipe corrosion monitoring device includes a steam introduction unit for introducing thereinto steam flowing through a metal pipe; and a corrosion testing unit provided in the steam introduction unit, characterized in that the steam introduction unit is configured to generate condensed water by condensing some of the steam to create a simulated environment similar to an actual environment in the metal pipe and discharge the condensed water above a predetermined water level to the outside. The corrosion testing unit has one or more contact members that contact with a water line region around a water surface of the condensed water in the steam introduction unit, a water phase region on a condensed water side and a vapor phase region on a steam side, and is configured to be able to measure an electric resistance of the one or more contact members.

15 Claims, 6 Drawing Sheets

(56) References Cited

U.S. PATENT DOCUMENTS

| | | | |
|---|---|---|---|
| 5,896,034 A * | 4/1999 | Marshall | G01N 27/205 204/404 |
| 6,015,484 A * | 1/2000 | Martinchek | G01N 17/02 204/404 |
| 6,383,451 B1 | 5/2002 | Kim et al. | |
| 2012/0145187 A1 | 6/2012 | Abe et al. | |

FOREIGN PATENT DOCUMENTS

| | | |
|---|---|---|
| JP | 2008-128732 | 6/2008 |
| JP | 2008-128783 | 6/2008 |
| JP | 2009-144952 | 7/2009 |

* cited by examiner

METAL PIPE CORROSION MONITORING DEVICE AND USE THEREOF

TECHNICAL FIELD

The present invention relates to a metal pipe corrosion monitoring device and use thereof.

BACKGROUND ART

In a boiler generating steam, softened water or ion-exchange water is used as boiler water. According to circumstances, raw water (tap water, industrial water, underground water, river water, lake water, pond water, or the like) is used.

In a boiler steam and condensate system including such a boiler and a metal pipe (for example, a ferrous metal pipe) for distributing steam from the boiler, the steam generated by the boiler cools to be condensed water inside the metal pipe. In the case of condensed water having a higher carbonic acid concentration, the pH thereof decreases to facilitate progression of corrosion of an inside surface of the metal pipe. Progression of corrosion causes metal-loss in the metal pipe, which may lead to a through hole, a crack, and the like.

As Conventional Art 1 to monitor such corrosion of a metal pipe, there has been proposed a method of monitoring corrosion progression in a test piece placed in a test column formed of a transparent material (see Patent Document 1, for example). The method evaluates the corrosion state in a boiler condensate system by passing boiler condensate through the test column containing the test piece, and determining the state of the test piece based on external observation and the corrosion rate.

As Conventional Art 2 to monitor corrosion of a metal pipe, there has been proposed a method by using a boiler condensate system corrosion monitoring device according to an electric resistance method (see Patent Document 2, for example). The method uses a boiler condensate system corrosion monitoring device including a heat exchanger for cooling steam discharged from a boiler into condensed water, a test column to be completely filled with the condensed water and a super-fine metal wire placed in the test column. The method measures the electric resistance of the super-fine metal wire in the test column and evaluates the corrosion state in a boiler condensate system based on an electric resistance change.

RELATED ART DOCUMENTS

Patent Documents

Patent Document 1: Japanese Unexamined Patent Publication No. HEI 8(1996)-28803
Patent Document 2: Japanese Unexamined Patent Publication No. 2008-128783

SUMMARY OF THE INVENTION

Problems to be Solved by the Invention

In the corrosion evaluation methods of Conventional Arts 1 and 2, corrosion of a metal pipe is monitored on the assumption that carbonic acid gas, oxygen gas and the like are completely dissolved in the condensate.

However, an actual boiler steam and condensate system has a condensed water region, a steam region and a water line region between the condensed water region and the steam region. Accordingly, the migration rate and the abundance ratio according to the temperature and the like of each gas component such as carbonic acid gas or oxygen gas vary with each region, and the corrosion progression also varies with each region.

Thus, determination and evaluation of corrosion according to the conventional evaluation methods fail to reflect the actual environment in the metal pipe. Accordingly, measures, that is, selection of an agent (anticorrosion agent or corrosion inhibitor) to add to the boiler steam and condensate system, and determination of the addition amount thereof based on the conventional evaluation methods are not considered most appropriate.

In view of the above-described problem, the present invention has been made to provide a metal pipe corrosion monitoring device that allows corrosion state assessment reflecting an actual environment in a metal pipe and the use thereof.

Means for Solving the Problem

According to the present invention, therefore, there is provided a metal pipe corrosion monitoring device including: a steam introduction unit for introducing thereinto steam flowing through a metal pipe; and a corrosion testing unit provided in the steam introduction unit, wherein
the steam introduction unit is configured to generate condensed water by condensing some of the steam introduced thereinto to create a simulated environment similar to an actual environment in the metal pipe and discharge the condensed water above a predetermined water level to the outside, and
the corrosion testing unit has one or more contact members that contact with a water line region around a water surface of the condensed water in the steam introduction unit, a water phase region on a condensed water side with respect to the water line region and a vapor phase region on a steam side with respect to the water line region, and is configured to be able to measure an electric resistance of the one or more contact members.

According to another aspect of the present invention, there is provided use of the corrosion monitoring device in a system including a metal pipe through which steam flows, wherein the corrosion monitoring device is connected to the metal pipe to monitor corrosion of the metal pipe.

Effects of the Invention

According to the present invention, it is possible to stably reproduce the actual environment in the metal pipe having the water phase region, the water line region and the vapor phase region, and thus it is possible to perform corrosion monitoring reflecting the actual environment in the metal pipe. That is, it is possible to measure the electric resistance of the one or more contact members that contact with the water phase region, the water line region and the vapor phase region in the steam introduction unit, and thus it is possible to assess which region in the metal pipe has the severest corrosion based on an electric resistance change.

As a result, it is possible to accurately assess, and accurately determine and evaluate the corrosion state in the actual environment (the water phase region, the water line region and the vapor phase region) in the current metal pipe, and at the same time, it is possible to take the most appropriate measures against the corrosion state at the right time. Specifically, it is possible to select the most appropriate agent (anticorrosion agent or corrosion inhibitor) to add to the boiler steam and condensate system, and determine the addition amount thereof promptly, leading to extension of the life of the boiler steam and condensate system.

Here, the term "metal pipe" as used in the present invention refers to a metal pipe for steam circulation included in various systems involving steam circulation. The material of the metal pipe is not particularly limited, and typical examples thereof include ferrous metals such as stainless steel and carbon steel.

Accordingly, the corrosion monitoring device of the present invention can be applied not only to boiler steam and condensate systems but also to all systems including a metal pipe through which steam flows. For example, the corrosion monitoring device of the present invention can be applied to a cooling water system for cooling in metal molding since in a metal pipe of such a cooling water system, cooling water is subjected to heat exchange at high temperature to come to a boil, and a water phase region, a water line region and a vapor phase region are generated.

BRIEF DESCRIPTION OF THE DRAWINGS

FIG. 5 (B) is a schematic left-side sectional view showing the internal structure of the corrosion monitoring device of Embodiment 3.

MODE FOR CARRYING OUT THE INVENTION

Figure 1:
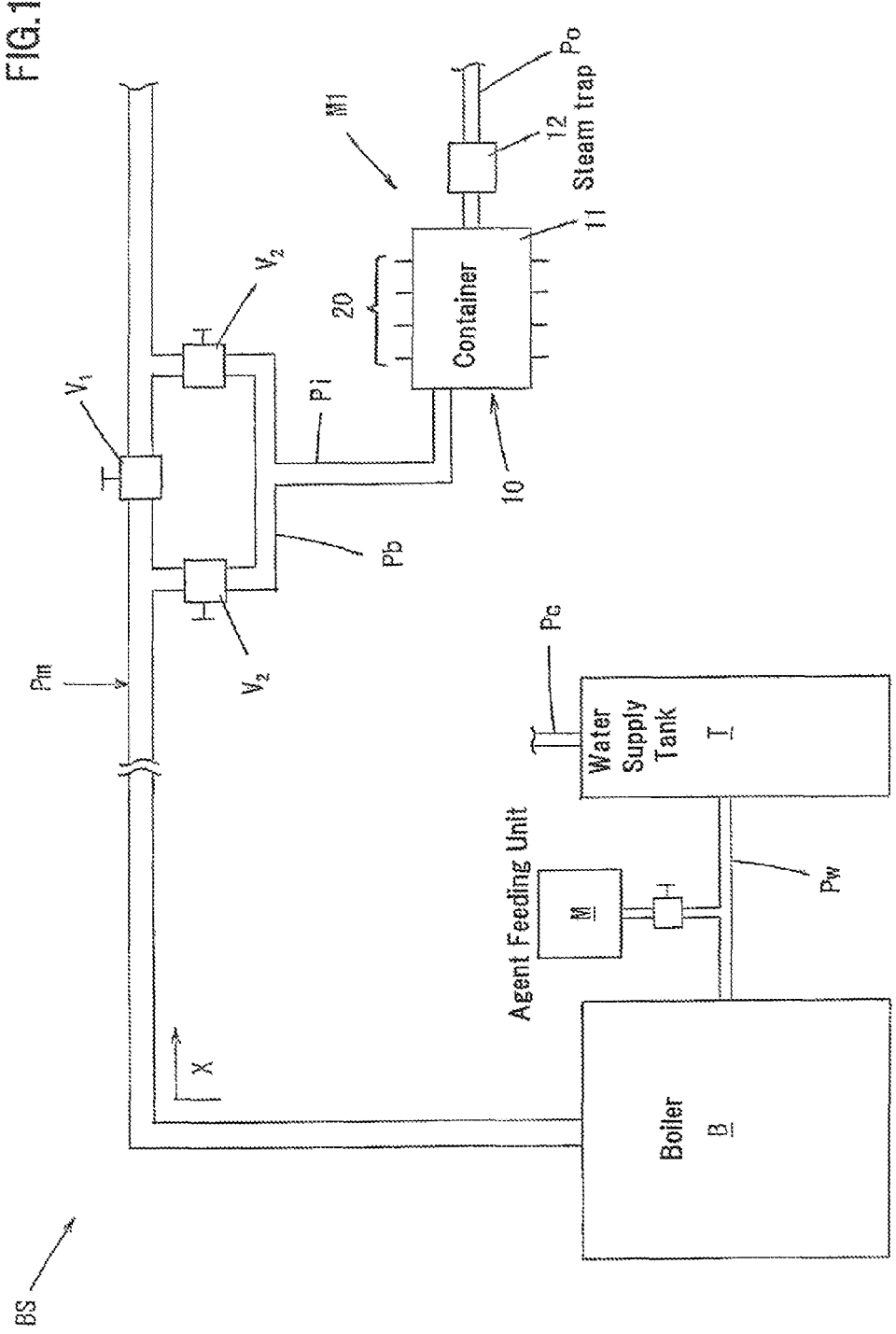
FIG. 1 is a diagram illustrating Embodiment 1 of a metal pipe corrosion monitoring device of the present invention in use.

A metal pipe corrosion monitoring device of the present invention includes: a steam introduction unit for introducing thereinto steam (water vapor) flowing through a metal pipe; and a corrosion testing unit provided in the steam introduction unit.

The steam introduction unit is configured to generate condensed water by condensing some of the steam introduced thereinto to create a simulated environment similar to an actual environment in the metal pipe and discharge the condensed water above a predetermined water level to the outside.

The corrosion testing unit has one or more contact members that contact with a water line region around a water surface of the condensed water in the steam introduction unit, a water phase region on a condensed water side with respect to the water line region and a vapor phase region on a steam side with respect to the water line region, and is configured to be able to measure an electric resistance of the one or more contact members.

The corrosion monitoring device of the present invention may be configured as follows.

(1) The steam introduction unit may have a steam trap on a side where the condensed water is discharged.

According to the configuration, the condensed water in the steam introduction unit can be readily maintained at a constant water level.

(2) The steam introduction unit may have a connection pipe to be connected to the metal pipe directly or via a by-pass pipe.

According to the configuration, the corrosion monitoring device is readily connected to the metal pipe.

(3) The steam introduction unit may include: a container for containing the corrosion testing unit, the container having an introduction port; and a holder being connected with the connection pipe and having a mounting recess in which the container is detachably fitted.

According to the configuration, the container can be detached from the holder, and therefore the old contact member can be quickly and readily replaced with new one without being removed from the container.

(4) The corrosion testing unit may include an electric circuit unit for detecting and displaying an electric resistance value of the one or more contact members.

According to the configuration, the corrosion monitoring on the metal pipe can be readily performed. The electric circuit unit may be fixed or portable.

(5) The corrosion testing unit may include a reference resistance measuring member having a conductive member covered with an insulative covering member so as not to be exposed in the steam introduction unit.

According to the configuration, the electric resistance values of the contact members, which change with temperature, can be corrected by measuring an electric resistance value of the conductive member of the reference resistance measuring member, which changes only with the temperature factor. The electric resistance values of the contact members can be corrected also by measuring the temperature inside the steam introduction unit.

(6) The corrosion testing unit may have three separate contact members of which one contact member contacts only with the water phase region, another contact member contacts only with the water line region and the other contact member contacts only with the vapor phase region. In this case, the separate contact members can be each formed by, for example, covering a portion of a bar-shaped conductive member with an insulative covering member in such a manner that the contact members contact only with the water phase region, only with the water line region and only with the vapor phase region, respectively.

(7) The corrosion testing unit may have one integrated contact member that contacts with the water phase region, the water line region and the vapor phase region. In this case, a sheet of thin-film-shaped conductive member having a length extending from the water phase region to the vapor phase region can be used as the integrated contact member, for example.

According to another aspect of the present invention, there is provided a contact member to be used in the metal pipe corrosion monitoring device according to (6) above. In this case, the contact member includes a bar-shaped conductive member, for example.

Alternatively, there is provided a contact member to be used in the metal pipe corrosion monitoring device according to (7) above. In this case, the contact member includes a thin-film-shaped conductive member, for example.

Preferably, the bar-shaped conductive member and the thin-film-shaped conductive member are formed of a material similar to the material of the metal pipe for achieving corrosion monitoring that reflects the actual environment in the metal pipe. Particularly preferably, they are formed of the same material as the material of the metal pipe.

Hereinafter, embodiments of the metal pipe corrosion monitoring device of the present invention will be described in detail with reference to the drawings. However, the present invention is not limited thereto.

Embodiment 1

Figure 2:
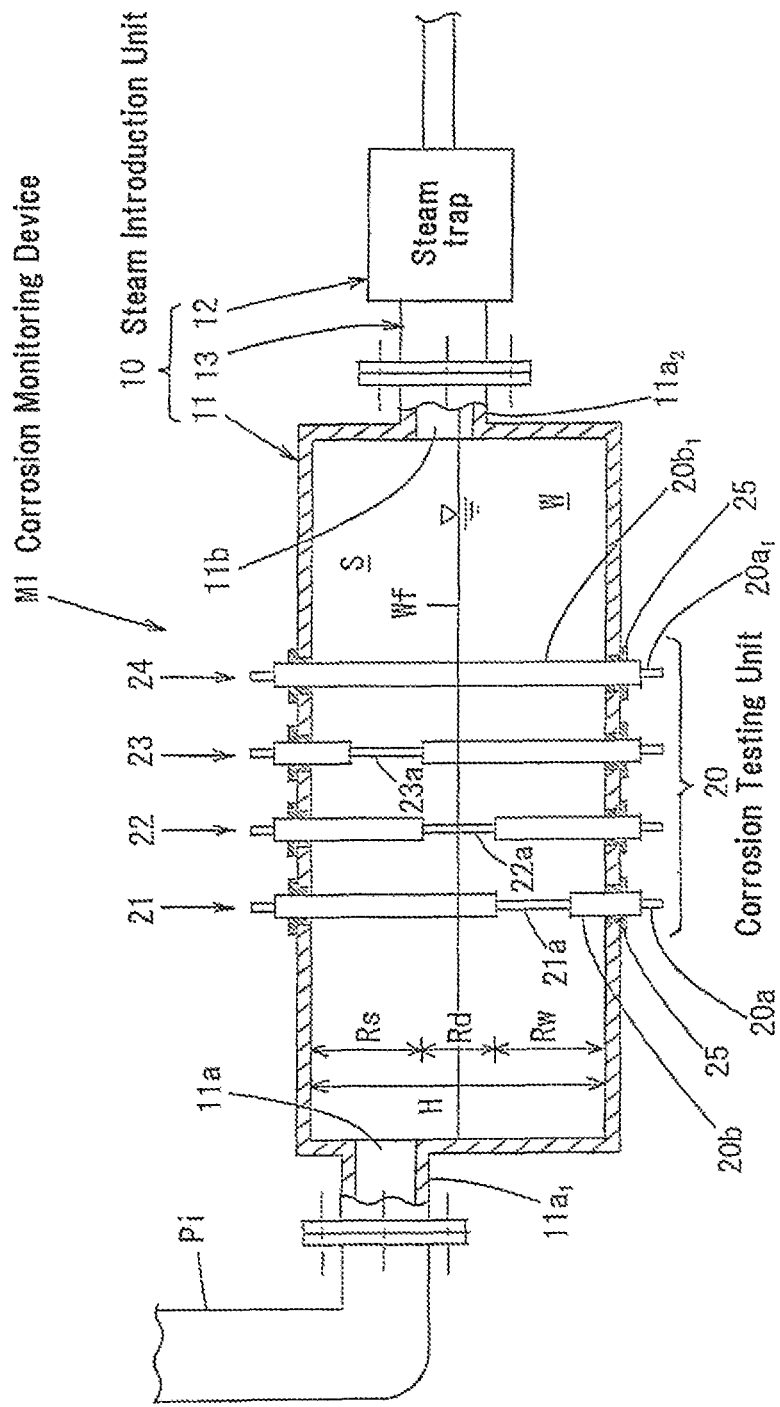
FIG. 2 is a schematic front sectional view showing an internal structure of the corrosion monitoring device of Embodiment 1.
Figure 3:
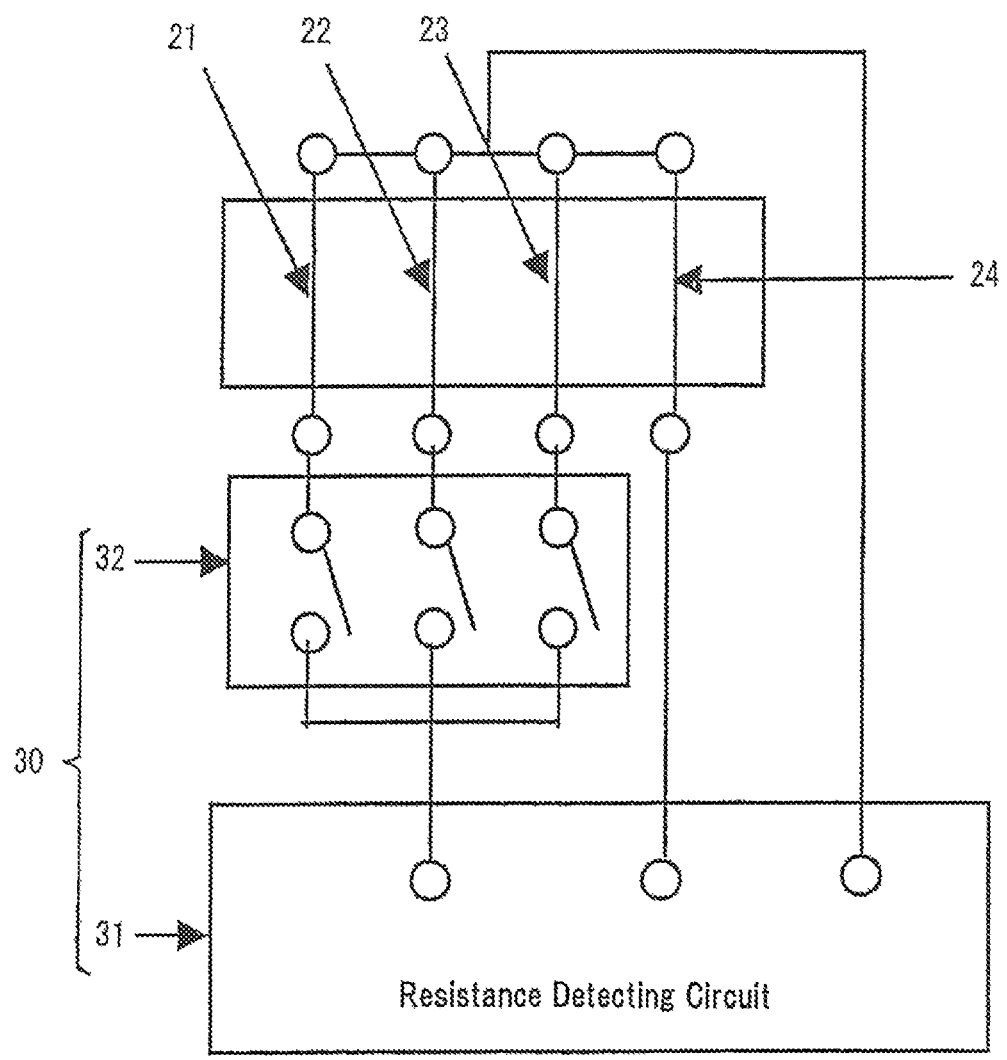
FIG. 3 is a circuit diagram showing an example of an electric circuit unit of the corrosion monitoring device of Embodiment 1.

FIG. 1 is a diagram illustrating Embodiment 1 of the metal pipe corrosion monitoring device of the present invention in use. FIG. 2 is a schematic front sectional view showing an internal structure of the corrosion monitoring device of Embodiment 1. FIG. 3 is a circuit diagram showing an example of an electric circuit unit of the corrosion monitoring device of Embodiment 1.

As shown in FIG. 1, a metal pipe corrosion monitoring device M1 is a device that is provided to a boiler steam and condensate system BS to monitor corrosion of a metal pipe (steam piping) Pm.

In the case of Embodiment 1, the boiler steam and condensate system BS includes: a boiler B; a water supply tank T for supplying boiler water to a boiler B through a water supply pipe Pw; an agent feeding unit M connected to the water supply pipe Pw; and the metal pipe Pm for sending steam generated in the boiler B to a steam supply destination, not shown, wherein condensed water obtained through condensation of the steam in the metal pipe Pm is returned to the water supply tank T through a condensate pipe Pc.

The corrosion monitoring device M1 is connected to a desired position in the metal pipe Pm. In the case of Embodiment 1, a by-pass pipe Pb having a pair of valves $V_2$ is connected to an upstream side and a downstream side of a valve $V_1$ of the metal pipe Pm, and the corrosion monitoring device M1 is connected to the by-pass pipe Pb via an introduction pipe Pi.

While the case in which the corrosion monitoring device M1 is disposed in a position below the metal pipe Pm is exemplified in Embodiment 1, the corrosion monitoring device M1 may be disposed in a position at the same level as or above the metal pipe Pm.

In the metal pipe Pm, not only steam but also condensed water obtained through condensation of the steam is circulated, and a vapor phase region, a water phase region and a water line region between the vapor phase region and the water phase region exist inside the metal pipe Pm. In FIG. 1, an arrow X represents a direction in which the steam flows.

The corrosion monitoring device M1 of the present invention is configured to assess the corrosion state in each region in the metal pipe Pm by reproducing a simulated environment similar to an actual environment including the vapor phase region, the water phase region and the water line region existing in the metal pipe Pm and monitoring electric resistance changes of contact members to be described later provided in the corrosion monitoring device M1.

The corrosion monitoring device M1 includes a steam introduction unit 10 having an introduction port 11a for introducing the steam flowing through the metal pipe Pm into the introduction unit, a corrosion testing unit 20 provided in the steam introduction unit 10 and an electric circuit unit 30.

The steam introduction unit 10 is configured to generate condensed water W by condensing some of the steam introduced thereinto and discharge the condensed water W above a predetermined water level (position of a water surface Wf) to the outside through a discharge pipe Po. Specifically, the steam introduction unit 10 includes a container 11 having the introduction port 11a and a discharge port 11b, a steam trap 12, and a connection pipe 13 for connecting the discharge port 11b of the container 11 with an introduction port of the steam trap 12.

Preferably, the container 11 is formed of a material having pressure resistance, heat resistance and corrosion resistance, and examples of the material include stainless steel and ceramic.

In Embodiment 1, the discharge port 11b is provided in a position of the predetermined water level in the container 11 in order to discharge to the outside the condensed water W above the predetermined water level in the container 11 and steam S introduced, and the introduction port 11a is provided in a position above the position of the predetermined water level. The container 11 has a communicating pipe $11a_1$ communicating with the introduction port 11a and a communicating pipe $11a2$ communicating with the discharge port 11b. The communicating pipe $11a_1$ and the introduction pipe Pi at an upstream side are connected in an airtight manner, and the communicating pipe $11a_2$ and the connection pipe 13 at a downstream side are connected in an airtight manner.

The container 11 is formed into a cylindrical shape or a squared cylindrical shape. A top end and a bottom end of a circumferential wall of the container 11 has through holes for receiving a plurality of contact members of the corrosion testing unit 20 to be described later.

The corrosion testing unit 20 has a second contact member 22a that contacts with a water line region Rd around the water surface Wf of the condensed water W in the steam introduction unit 10, a first contact member 21a that contacts with a water phase region (condensed water region) Rw on a condensed water W side with respect to the water line region Rd and a third contact member 23a that contacts with a vapor phase region (steam region) Rs on a steam S side with respect to the water line region Rd. The electric resistance of the first, second and third contact members 21a, 22a and 23a can be measured separately.

More specifically, in the case of Embodiment 1, the first contact member 21a is made of a bar-shaped conductive member 20a, and the bar-shaped conductive member 20a is covered with an insulative covering member 20b in such a manner that the bar-shaped conductive member 20a is exposed only to the water phase region Rw, thereby forming a first testing member 21. That is, in the present description, a portion of the first testing member 21 where the bar-shaped conductive member 20a is exposed is referred to as the first contact member 21a.

Likewise, the second contact member 22a is also made of a bar-shaped conductive member 20a, and the bar-shaped conductive member 20a is covered with an insulative covering member 20b in such a manner that the bar-shaped conductive member 20a is exposed only to the water line region Rd, thereby forming a second testing member 22. That is, in the present description, a portion of the second testing member 22 where the bar-shaped conductive member 20a is exposed is referred to as the second contact member 22a.

The third contact member 23a is also made of a bar-shaped conductive member 20a, and the bar-shaped conductive member 20a is covered with an insulative covering member 20b in such a manner that the bar-shaped conductive member 20a is exposed only to the vapor phase region Rs, thereby forming a third testing member 23. That is, in the present description, a portion of the third testing member 23 where the bar-shaped conductive member 20a is exposed is referred to as the third contact member 23a.

Furthermore, the first to third contact members 21a to 23a (exposed portions of the bar-shaped conductive members 20a) are formed in accordance with the same standards, and the lengths thereof are set to be substantially equal. The lengths of the first to third contact members 21a to 23a, the same or different, do not affect the measurement of the electric resistance. However, the equal lengths (equal surface areas) provide equal contingencies of corrosion, allowing a more adequate corrosion test.

"The same standards" as used herein encompass material, cross-sectional shape, cross-sectional area and surface condition.

In the case of Embodiment 1, the linear dimensions of the first to third contact members 21a to 23a are set so as to be the same as a dimension of the water line region Rd in a vertical direction on the assumption that the middle of the water line region Rd in the vertical direction is the position of the water surface Wf.

In the case of Embodiment 1, furthermore, examples of inner diameters of the metal pipe Pm and the by-pass pipe Pb include, but are not limited to, approximately 105 mm, examples of a width dimension H of the inner space of the container 11 in the vertical direction include, but are not limited to, approximately 105 to 154 mm, and examples of the dimension of the water line region Rd in the vertical direction include, but are not limited to, approximately 30 to 50 mm.

The material of the conductive members 20a is not particularly limited as long as it is a metallic material that can be measured for electric resistance. When the material of the metal pipe Pm in the boiler steam and condensate system BS is a ferrous metal, it is desirable that the material of the conductive members 20a is also a ferrous metal. The ferrous metal as used herein refers to a metal containing iron as a main component (preferably 50% by weight or more), although the ratio of iron in the metal is not limited.

The shape of the conductive members 20a is not particularly limited as long as it allows the measurement of the electric resistance and is desirably a shape that allows uniform corrosion over the whole area. Examples of the shape include a columnar shape and a thin film shape (tape shape).

The cross-sectional area and the total length of the conductive members 20a are not particularly limited. Preferably, the cross-sectional area is approximately 0.008 to 0.8 $mm^2$, and the length is approximately 10 to 1000 mm since a too large cross-sectional area and a too short length of the testing members cause the conductive members 20a to show a so small electric resistance change for the corrosion amount that it is difficult to determine the corrosion.

Preferably, the material of the insulative covering members 20b is an insulating material having heat resistance, and examples thereof include synthetic resins and the like such as fluororesin and polyimide.

The steam trap 12 usable in the present invention is not particularly limited, and examples thereof include those of disk type, bucket type, bimetal type, bellows type and float type.

In the corrosion monitoring device of the present invention, the electric resistance of the conductive members 20a increases with temperature rise. In Embodiment 1, therefore, the corrosion testing unit 20 further includes a reference resistance measuring member 24.

The reference resistance measuring member 24 has a reference conductive member $20a_1$ formed in accordance with the same standards as the conductive members 20a and an insulative covering member $20b_1$ for covering the reference conductive member $20a_1$ in such a manner that the reference conductive member $20a_1$ is not exposed in the container 11. Thus, the reference resistance measuring member 24 can measure the electric resistance of the reference conductive member $20a_1$.

The reference resistance measuring member 24 allows accurate monitoring of electric resistance changes due to corrosion in the respective conductive members 20a of the first to third testing members 21 to 23 by comparing a measured value of the electric resistance of each conductive member 20a with a measured value of the electric resistance of the reference conductive member $20a_1$ since the electric resistance of the reference conductive member $20a_1$ does not change due to any other factors than temperature.

In the case of Embodiment 1, the first testing member 21 is formed from the conductive member 20a longer than a dimension of the container 11 in the vertical direction and the insulative covering member 20b covering the conductive member 20a in such a manner that only opposite ends and a portion in the water phase region Rw of the conductive member 20a are exposed. The first testing member 21 is attached to the container 11 by inserting the first testing member 21 into the container 11 in such a manner that opposite ends of the first testing member 21 project outside from the through holes and pushing fluororesin seals 25 put around the opposite ends of the first testing member 21 in the through holes, for example. Thereby, the first testing member 21 can be fixed to the container 11 in an airtight manner. Each fluororesin seal 25 may be held in position by a metal plate attached to the outer circumference of the container 11, for example, in order to prevent the fluororesin 25 from coming out of the through hole due to the inner pressure of the container 11.

Alternatively, the first testing member 21 may be attached to the container 11 by a structure, for example, in which each through hole of the container 11 is a screw hole, the conductive member 20a is inserted in a cylindrical member having a male screw that fits the screw hole via a fluororesin seal, and the male screw is screwed in the screw hole via a sealing tape.

In the second and third testing members 22 and 23, likewise, the conductive members 20a in accordance with the same standards as the conductive member 20a of the first testing member 21 are used, and each conductive member 20a is covered with each insulative covering member 20b in such a manner that only opposite ends and a portion in the water line region Rd or only opposite ends and a portion in the vapor phase region Rs are exposed. The second and third testing members 22 and 23 are attached to the container 11 in the same manner as in the first testing member 21.

In the reference resistance measuring member 24, likewise, the conductive member $20a_1$ in accordance with the same standards as the conductive member 20a of the first testing member 21 is used, and the conductive member $20a_1$ is covered with the insulative covering member $20b_1$ in such a manner that only opposite ends are exposed. The reference resistance measuring member 24 is attached to the container 11 in the same manner as in the first testing member 21.

The electric circuit unit 30 shown in FIG. 3 includes: a resistance detecting circuit 31 electrically connected to the opposite ends of the respective conductive members 20a of the first to third testing members 21 to 23 and to the opposite ends of the conductive member $20a_1$ of the reference resistance measuring member 24; a switching circuit 32; and a power source, not shown.

The resistance detecting circuit 31 is provided with a non-inverting amplifying circuit, not shown, a measurement section and a display section. The resistance detecting circuit 31 displays on the display section electric resistance values (corrected electric resistance values) obtained through individual and automatic temperature compensation of electric resistance values of the respective conductive members 20a of the first to third testing members 21 to 23 by the non-inverting amplifying circuit.

As shown in FIGS. 1 and 2, during operation of the boiler steam and condensate system of Embodiment 1 having the above-described configuration, the steam generated by the boiler B is continuously supplied to a steam supply destination (a heat exchanger, for example), not shown, through the metal pipe Pm without going through the by-pass pipe Pb, while the valve $V_1$ of the metal pipe Pm is opened and the pair of valves $V_2$ of the by-pass pipe Pb are closed.

For monitoring corrosion of the metal pipe Pm, the valve $V_1$ of the metal pipe Pm is closed and the pair of valves $V_2$ of the by-pass pipe Pb are opened, and thereby the steam from the boiler B is continuously supplied to the steam supply destination, not shown, through the metal pipe Pm and the by-pass pipe Pb, and some of the steam flowing through the by-pass pipe Pb and condensed water obtained through condensation of the steam is introduced into the container 11 of the corrosion monitoring device M1 of the present invention through the introduction pipe Pi. Consequently, the condensed water W is accumulated in the container 11, and the condensed water W above the predetermined water level in the container 11 is introduced into the steam trap 12 through the connection pipe 13 and discharged to the outside by the steam trap 12.

Meanwhile, during operation of the boiler steam and condensate system of Embodiment 1, the first to third contact members 21a to 23a in the container 11 of the corrosion monitoring device M1 of the present invention are gradually corroded as being in contact with the water phase region Rw, the water line region Rd and the vapor phase region Rs as shown in FIGS. 2 and 3.

For monitoring progression of the corrosion, the switching circuit 32 of the electric circuit unit 30 is operated to form a test circuit with one of the first to third testing members and the reference resistance measuring member 24, and a current is applied to the test circuit. Then, the resistance values of the first to third testing members are measured with the resistance detecting circuit 31. The measured values are compensated for temperature by the reference resistance measuring member 24 as described above.

By individually and continuously monitoring the electric resistance values of the first to third testing members 21 to 23 as described above, it is possible to observe the electric resistance changes in the testing members, and thus it is possible to know which of the contact members 21a to 23a of the first to third testing members 21 to 23 increases in electric resistance fastest, that is, which has the fastest corrosion progression rate.

If a result of such monitoring shows that the contact member 22a of the second testing member 22 has the fastest corrosion progression rate, it is inferred that the metal pipe Pm is corroded in the water line region most severely. As a result, appropriate measures to inhibit the corrosion progression in the water line region of the metal pipe Pm or to prevent further corrosion progression can be taken.

That is, an agent suitable for inhibiting or preventing the corrosion progression in the water line region of the metal pipe Pm is selected and the addition amount thereof is determined based on the result of the corrosion monitoring, and thus an appropriate amount of the agent can be sent into the metal pipe Pm of the boiler steam and condensate system BS, for example.

In the case of Embodiment 1, an appropriate amount of a liquid agent is fed from the agent feeding unit M to the boiler water flowing through the water supply pipe Pw, and the agent joins the steam to flow from the boiler B through the metal pipe Pm into the container 11 of the corrosion monitoring device M1. Thereby, the corrosion progression in the internal surface of the metal pipe Pm and in the contact members 21a to 23a in the container 11 is inhibited. The inhibition of the corrosion progression can be perceived by continuously performing the above-described corrosion monitoring and confirming that the rate of increase in the electric resistance of the first to third testing members 21 to 23 has been reduced.

Once the corrosion progression is to a certain extent, the contact members 21a to 23a (conductive members 20a) of the first to third testing members 21 to 23 need to be replaced with new ones. During operation of the boiler steam and condensate system BS, the replacement is performed by opening the valve $V_1$ of the metal pipe Pm and closing the valves $V_2$ on the upstream side and the downstream side of the by-pass pipe Pb to ensure safety so that the steam will not flow into the container 11, and then removing the first to third testing members 21 to 23 from the container 11 and attaching new ones to the container 11.

Embodiment 2

Figure 4:
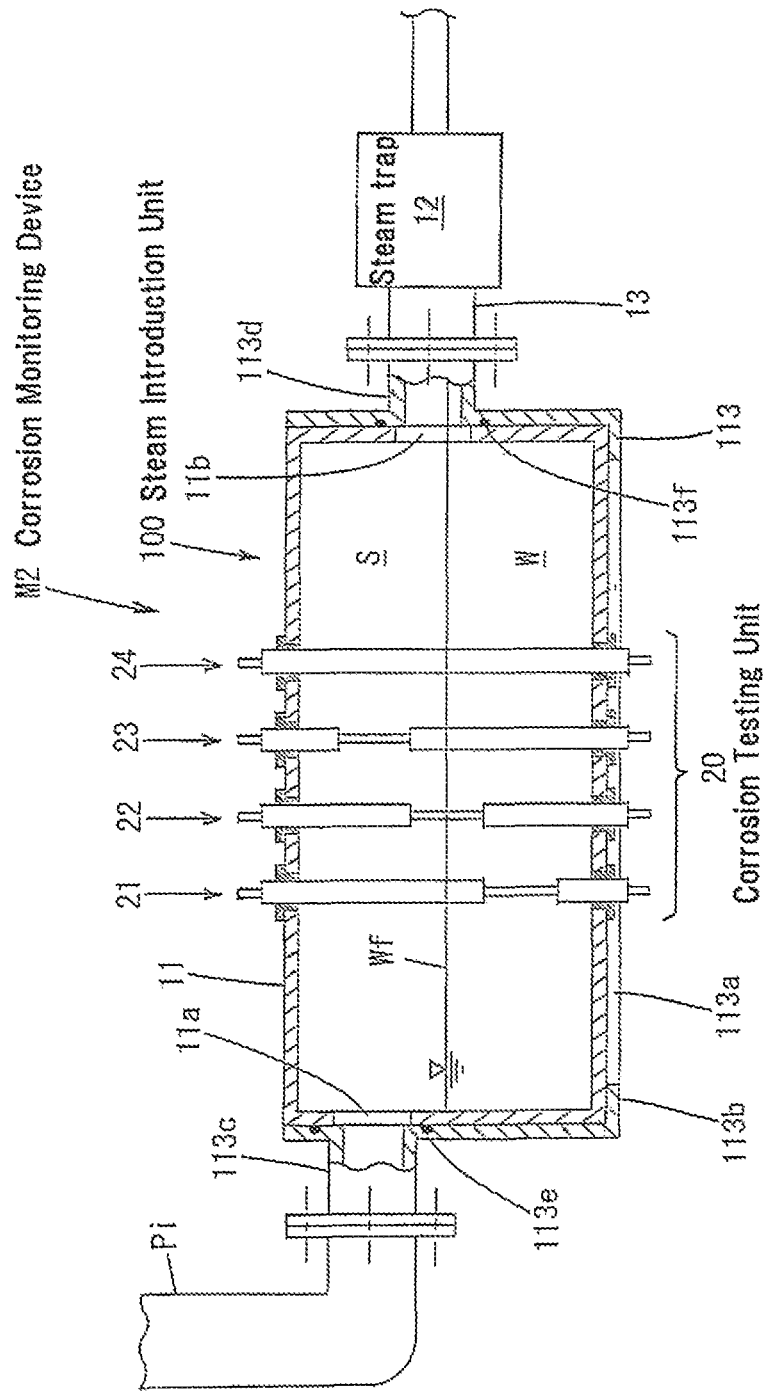
FIG. 4 is a schematic front sectional view showing an internal structure of a corrosion monitoring device of Embodiment 2.

FIG. 4 is a schematic front sectional view showing an internal structure of a corrosion monitoring device of Embodiment 2. In FIG. 4, the same components as those in FIG. 2 are represented by the same reference numerals.

While the corrosion monitoring device M1 of Embodiment 1 has a configuration in which the first to third testing members 21 to 23 are removed from the container 11 and replaced with new ones, the corrosion monitoring device M2 of Embodiment 2 has a configuration in which the first to third testing members 21 to 23 are removed while remaining in the container 11.

Specifically, in the corrosion monitoring device M2 of Embodiment 2, a steam introduction unit 100 has a container 11 formed into a shape of a square cartridge (squared cylindrical shape), a steam trap 12 connected to the container 11, a holder 113 for detachably holding the container 11 and a connection pipe 13 for connecting the container 11 with the steam trap 12 via the holder 113. Thus, Embodiment 2 is greatly different from Embodiment 1 in that it includes the holder 113. In Embodiment 2, the other configurations are the same as those of Embodiment 1. Hereinafter, differences of Embodiment 2 from Embodiment 1 will be mainly described.

The holder 113 in Embodiment 2 has a holder main body 113a having a mounting recess of substantially the same size as the container 11 and communicating pipes 113c and 113d provided to the holder main body 113a.

The holder main body 113a is formed into a shape of a quadrate box having upper and lower openings 113a, and the internal space thereof constitutes the mounting recess. The bottom of the mounting recess is provided with an inward rim 113b along the lower opening 113a. The container 11 is fitted in the mounting recess of the holder main body 113a through the upper opening.

Opposing walls of the holder main body 113a on an upstream side and a downstream side are provided with the communicating pipes 113c and 113d communicating with an introduction port 11a and a discharge port 11b of the container 11 in place, and O-rings 113e and 113f. The communicating pipe 113c on the upstream side is connected to a by-pass pipe Pb on the upstream side in an airtight manner, and the communicating pipe 113d on the downstream side is connected to the connection pipe 113b in an airtight manner.

According to the corrosion monitoring device M2 of Embodiment 2, the replacement of the first to third testing members 21 to 23 is performed by drawing upward the container 11 out of the holder main body 113a and mounting in the holder 113a the container in which new first to third testing members and reference resistance measuring member have been preliminarily set. Thus, the replacement can be performed readily and quickly. Alternatively, the old first to third testing members 21 to 23 from the container 11 taken out of the holder 113a may be replaced with new ones, and then the container 11 may be mounted in the holder main body 113a.

According to Embodiment 2, the replacement can be performed readily and safely when the corrosion monitoring device M2 needs to be installed in a high place.

Embodiment 3

Figure 5A:
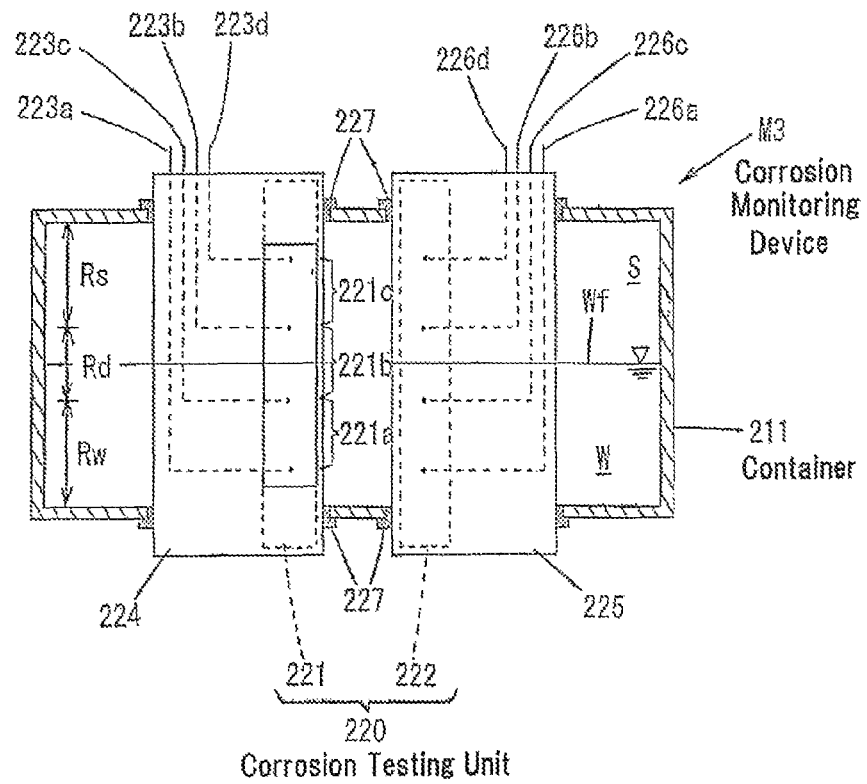
FIG. 5 (A) is a schematic front sectional view showing an internal structure of a corrosion monitoring device of Embodiment 3.
Figure 5B:
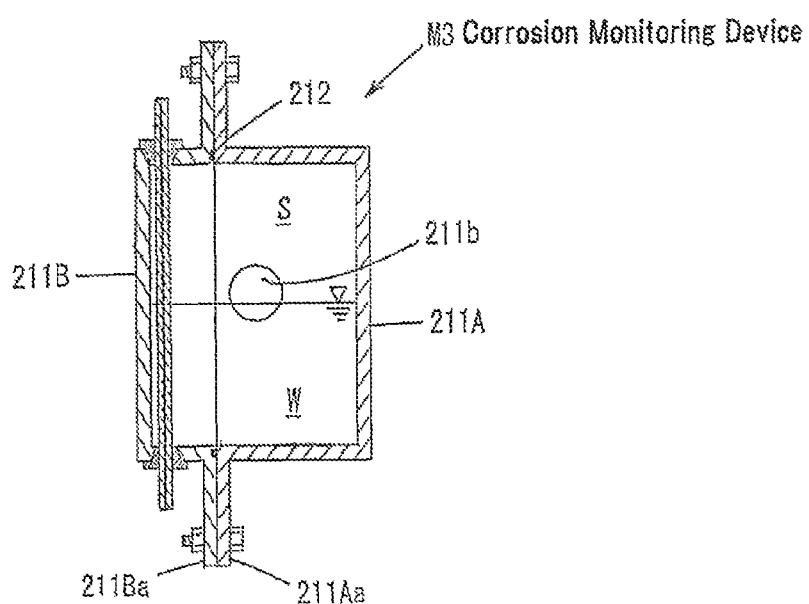

FIG. 5 (A) is a schematic front sectional view showing an internal structure of a corrosion monitoring device of Embodiment 3, and FIG. 5 (B) is a schematic left-side sectional view showing the internal structure of the corrosion monitoring device of Embodiment 3. In FIGS. 5 (A) and 5 (B), the same components as those in FIG. 2 are represented by the same reference numerals.

The corrosion monitoring device M3 of Embodiment 3 is different from the device of Embodiment 1 in a configuration of a container 211, a configuration of a corrosion testing unit 220 and a configuration of an electric circuit unit, not shown, and the other configurations in Embodiment 3 are the same as those in Embodiment 1. Hereinafter, differences of Embodiment 3 from Embodiment 1 will be mainly described.

The container 211 has a back portion 211B and a front portion 211A having an introduction port and a discharge port 211b, and is formed into a squared cylindrical shape by coupling flanges 211Aa and 211Ba provided on outer peripheries of the front and back portions by bolt-and-nut connection. Joint surfaces of the front portion 211A and the back portion 211B are provided with a sealing member 212.

Opposing upper and lower walls of the back portion 211B each have an elongated through hole for attaching the corrosion testing unit 220 to be described later to the container 211.

In the corrosion testing unit 220, a testing member has a contact member 221a in a water phase region, a contact member 221b in a water line region and a contact member 221c in a vapor phase region, and the contact members are formed of one thin-film-shaped (tape-shaped) conductive member 221 exposed to the water phase region Rw, the water line region Rd and the vapor phase region Rs.

The corrosion testing unit 220 further includes: a first lead wire 223a electrically connected to a first boundary between the contact member 221a in the water phase region and the contact member 221b in the water line region in the conductive member 221, and guided to the outside; a second lead wire 223b electrically connected to a second boundary between the contact member 221b in the water line region and the contact member 221c in the vapor phase region in the conductive member 221, and guided to the outside; a third lead wire 223c electrically connected to an end of the contact member 221a in the water phase region and guided to the outside, the end being a predetermined dimension away from the first boundary in the conductive member 221; a forth lead wire 223d electrically connected to an end of the contact member 221c in the vapor phase region and guided to the outside, the end being a predetermined dimension away from the second boundary of the conductive member 221; and an insulative covering member 224 for covering the first to forth lead wires 223a to 223d.

Specifically, the insulative covering member 224 is made of a resin sheet or a rubber sheet having heat resistance, and one sheet of the conductive member 224 is sandwiched between two sheets of the insulative covering member 224 or in one sheet of the insulative covering member 224 folded in half, and a portion of the insulative covering member 224 is cut out to form a window in such a manner that one surface of the conductive member 224 is exposed. The first to fourth lead wires 223a to 223d are also sandwiched by the insulative covering member 224 while their ends on one side are placed between the conductive member 221 and the insulative covering member 224 and independently soldered to the above-described positions in the conductive member 221.

Ends of the first to fourth lead wires 223a to 223d on the other side are exposed to the outside from an upper end of the insulative covering member 224. The lead wires 223a to 223d may be corroded if condensed water W or steam S gets between mating surfaces of the insulative covering member 224. In this case, it is difficult to accurately measure the electric resistance of the conductive member 221. The mating surfaces of the insulative covering member 224 may therefore be bonded together with an adhesive, and the lead wires 223a to 223d may be further covered with insulative covering members separately.

In the case of Embodiment 3, a conductive member 222 in accordance with the same standards as the conductive member 221 and fifth to eighth lead wires 226a to 226d are covered with a covering member 225 in the same manner as in the conductive member 221 except that the conductive member 222 is not exposed, and ends of the fifth to eighth lead wires 226a to 226d on one side are electrically connected to the conductive member 222 and ends thereof on the other side are exposed to the outside in the same manner as in the first to forth lead wires 223a to 223d. Thus, a reference resistance measuring member is formed.

The insulative covering member 224 having therein the conductive member 221 and the first to fourth lead wires 223a to 223d, and the insulative covering member 225 having therein the conductive member 222 and the fifth to eighth lead wires 226a to 226d can be attached to the container 211 in an airtight manner by inserting them through the through holes of the container 211 and fixing them with rubber seals 227 in the same manner as in Embodiment 1.

As the electric circuit unit, not shown, in the case of the corrosion monitoring device M3 of Embodiment 3, the following electric circuit unit can be formed by applying the electric circuit unit 30 in Embodiment 1. That is, the electric circuit unit in Embodiment 3 can switch among the following (1) to (3) by a switching section.

(1) Form a test circuit including the first and third lead wires 223a and 223c, and the fifth and seventh lead wires 226a and 226c, apply a current to the test circuit, and measure an electric resistance value. In this case, the corrected electric resistance value of the contact member 221a exposed to the water phase region Rw can be obtained.

(2) Form a test circuit including the third and second lead wires 223c and 223b, and the seventh and sixth lead wires 226c and 226b, apply a current to the test circuit, and measure an electric resistance value. In this case, the corrected electric resistance value of the contact member 221b exposed to the water line region can be obtained.

(3) Form a test circuit including the second and forth lead wires 223b and 223d, and the sixth and eighth lead wires 226b and 226d, apply a current to the test circuit, and measure an electric resistance value. In this case, the corrected electric resistance value of the contact member 221c exposed to the vapor phase region can be obtained.

In the corrosion monitoring device M3 of Embodiment 3 having the above-described configuration, the conductive member 221 in the container 221 is gradually corroded as being exposed in the water phase region Rw, the water line region Rd and the vapor phase region Rs.

In order to monitor the progression of the corrosion, the above-described (1) to (3) are performed individually. Thus, it is possible to perform accurate corrosion monitoring in a plurality of environments (the water phase region Rw, the water line region Rd and the vapor phase region Rs) with one sheet of the conductive member 221. The sequencing of (1) to (3) is not particularly limited.

According to Embodiment 3, it is possible to individually observe the electric resistance changes compensated for temperature in the contact member 221a exposed to the water phase region, the contact member 221b exposed to the water line region and the contact member 221c exposed to the vapor phase region, and thus it is possible to know which of the contact members increases in electric resistance fastest, that is, which has the fastest corrosion progression rate.

Based on such monitoring, as in the case of Embodiment 1, the most appropriate measures can be taken for a region of the metal pipe Pm where corrosion is the severest, that is, the most suitable agent can be selected and the addition amount thereof can be determined, and thus an appropriate amount of the agent can be sent into the metal pipe Pm of the boiler steam and condensate system BS.

When the conductive member 221 needs to be replaced due to corrosion progression during operation of the boiler steam and condensate system BS, the valve $V_1$ of the metal pipe Pm is opened and the valves $V_2$ on the upstream side and the downstream side of the by-pass pipe Pb are closed to ensure safety so that the steam will not flow into the container 211 in the same manner as in Embodiment 1 (see FIG. 1), and then the back portion 211Ba of the container 211 is uncoupled from the front portion 211Aa, the conductive member 221 and the first to fourth lead wires 223a to 223d together with the insulative covering member 224 are removed from the back portion 211Ba, new ones are attached to the back portion 211Ba, and the container 211 is reassembled.

Other Embodiments

1. In the measurement of the electric resistance of the first to third testing members and the reference resistance measuring member 24 in Embodiment 1, terminals of a tester may be brought into electric contact with a pair of lead wires $30a_1$ and $30a_2$ in each measurement. The same applies to Embodiment 3.

2. In the case where the corrosion monitoring device of the present invention is installed to the boiler steam and condensate system BS that is shut down regularly (for example, shut down at night), the by-pass pipe Pb may be omitted, and the corrosion monitoring device may be installed directly to the metal pipe Pm.

3. In the reference resistance measuring member 222 in Embodiment 3 (FIG. 5 (A)), the sixth and seventh lead wires 226b and 226c may be omitted. In this case, the fifth and eighth lead wires 226a and 226d are always included in the test circuits.

4. The container 211 of Embodiment 3 may be formed into a cylindrical shape. In this case, a unit including the conductive member 221, the first to fourth lead wires 223a to 223d and the insulative covering member 224, and a unit including the conductive member 222, the fifth to eighth lead wires 226a to 226d and the insulative covering member 225 are disposed along a cylindrical inner surface of the container. Thus, the simulated environment in the cylindrical container can be more similar to the actual environment in the cylindrical metal pipe Pm.

EXAMPLES

Example 1

The corrosion monitoring device M1 of Embodiment 1 described with reference to FIGS. 2 and 3 was installed to the metal pipe Pm of the boiler steam and condensate system BS via the by-pass pipe Pb as shown in FIG. 1. The installation position of the corrosion monitoring device M1 was 10 m away from a boiler steam outlet.

Figure 6:
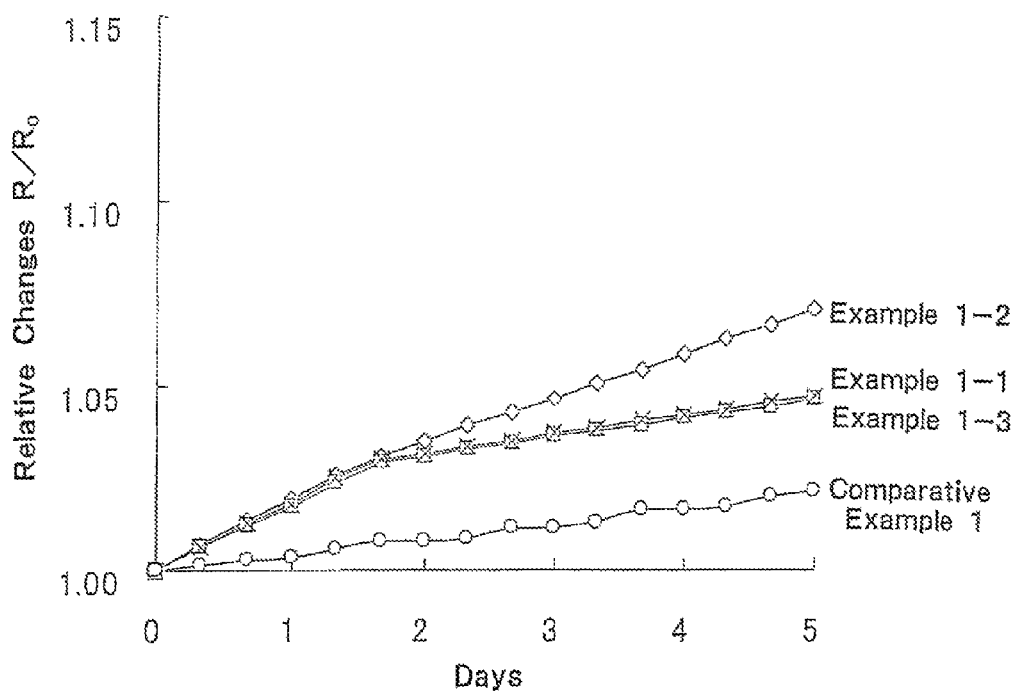
FIG. 6 is a graph showing results of metal pipe corrosion monitoring performed on Example 1 and Comparative Example 1 with the corrosion monitoring device of Embodiment 1.

The boiler steam and condensate system BS was then operated, and corrosion monitoring was carried out for five days by reproducing corrosion states of the water phase region, the water line region and the vapor phase region in the actual environment in the metal pipe Pm using the corrosion monitoring device M1, and then corrosion in the metal pipe Pm was evaluated and determined. Relative changes $R/R_0$ of the conductive members 20a obtained as a result are shown in FIG. 6. Here, $R_0$ is an electric resistance initial value of each conductive member 20a, and R is an electric resistance value of each conductive member 20a during the monitoring.

<Design Specifications of Corrosion Monitoring Device>
Material of container 11: SUS304
Width dimension H of inside of container 11 in vertical direction: 150 mm
Conductive members 20a of first to third testing members 21 to 23: columnar iron wire (material in accordance with JIS G 3522 A) having a length of 320 mm and a cross-sectional area of 0.03 $mm_2$ (diameter of 0.2 mm)
Insulative covering members 20b of first to third testing members 21 to 23: polyimide
Exposure dimension of conductive members 20a of first to third testing members 21 to 23: 50 mm
Reference resistance measuring member 24: prepared by entirely, except the opposite ends, covering the reference conductive member $20a_1$ in accordance with the same standards as the conductive members 20a with polyimide.
Resistance detection display section 30c of electric circuit unit 30: lock-in amplifier (LF5640, product by NF Circuit Design Block)
<Operational Specifications of Boiler Steam and Condensate System>
Steam: free from agents for corrosion prevention or corrosion inhibition for the metal pipe Pm
Temperature of condensed water W in container 11: approximately 180° C.
Inner pressure of pressure-resistant container of container 11: 1.3 MPa
<Method for Evaluation of Corrosion>
The corrosion was evaluated according to the relative change $R/R_0$, that is, changes of the electric resistance values of the first to third testing members 21 to 23 for the electric resistance measurement relative to their initial values.

In FIG. 6, Example 1-1 (line with square markers) represents the result of the first testing member 21, Example 1-2 (line with diamond markers) represents the result of the second testing member 22, and Example 1-3 (line with X markers) represents the result of the third testing member 23.

Comparative Example 1

The boiler condensate system corrosion monitoring device of Conventional Art 2 was installed to the metal pipe Pm of the boiler steam and condensate system BS via the by-pass pipe Pb in a position 10 m away from the boiler steam outlet in the same manner as in Example 1. Corrosion monitoring was carried out for five days under the same operation condition as in Example 1 (water temperature in the test column: approximately 25° C.), and then corrosion in the metal pipe Pm was evaluated and determined in the same manner as in Example 1. The result thereof is shown in FIG. 6.

In the boiler condensate system corrosion monitoring device of Conventional Art 2, a testing member for the electric resistance measurement used in the test column was the same as those of Example 1 except that it had a total length of 150 mm and it was entirely exposed to the water phase region.

Comparative Example 2

In place of the first to third testing members 21 to 23 in the corrosion monitoring device M1 of Example 1, test pieces as described below were set so as to be exposed to the water phase region Rw, the water line region Rd and the vapor phase region Rs, respectively, and the boiler steam and condensate system BS was operated under the same condition as in Example 1. Five days later, the operation was stopped and the test pieces were taken out to be determined for corrosion state by visual observation. The result thereof is shown in Table 1.

As each of the test pieces, a piece of a low carbon steel in accordance with JIS G 3141 (SPCC) having a size of 1 mm in thickness, 15 mm in width and 30 mm in length was prepared. Each test piece was entirely surface-finished with #400 abrasive paper and provided with two through holes having a diameter of 3 mm.

The corrosion states were determined as "A" when no deterioration was observed in the surface of the test piece, "B" when deterioration was observed in approximately 10 to 20% of the surface area of the test piece, and when deterioration was observed in 20% or more of the surface area of the test piece. The evaluation of Comparative Example 2 allows confirmation of the correlation with the result of Example 1.

Example 2

Figure 7:
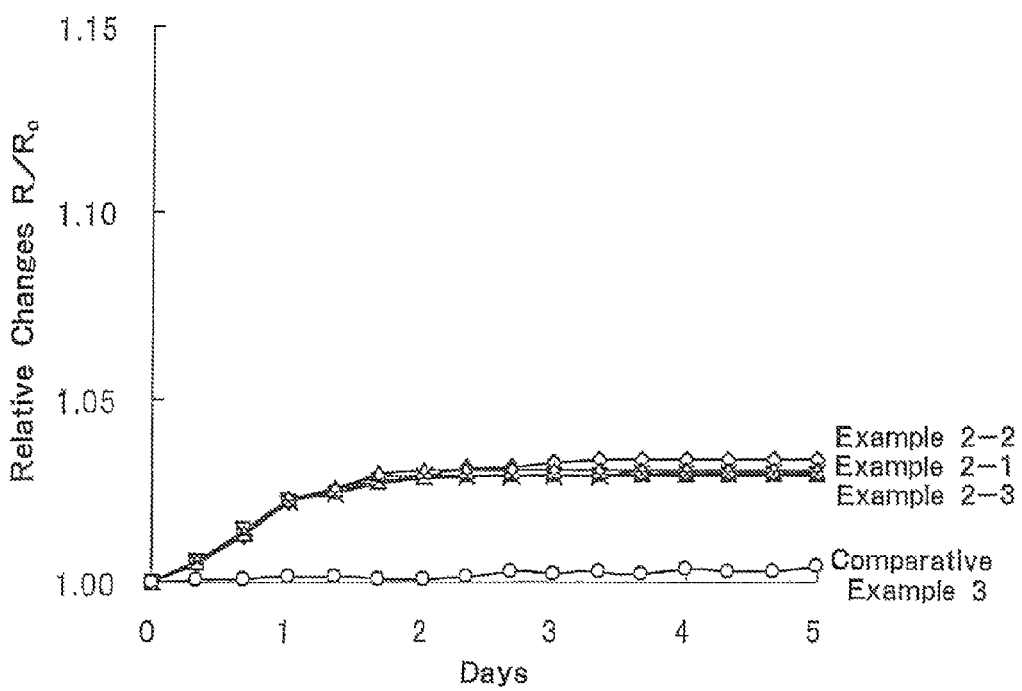
FIG. 7 is a graph showing results of metal pipe corrosion monitoring performed on Example 2 and Comparative Example 3 with the corrosion monitoring device of Embodiment 1.

Corrosion monitoring and examination was carried out in the same manner as in Example 1 except that volatile amine (trade name: MCC-H, product by Naigai Chemical Products Co., Ltd.) was introduced into the steam as an agent for corrosion prevention or corrosion inhibition for the metal pipe Pm so as to give a total amine concentration of 20 mg/L. The result thereof is shown in FIG. 7. In FIG. 7, Example 2-1 (line with square markers) represents the result of the first testing member 21, Example 2-2 (line with diamond markers) represents the result of the second testing member 22, and Example 2-3 (line with X markers) represents the result of the third testing member 23.

Comparative Example 3

Corrosion monitoring and examination was carried out in the same manner as in Comparative Example 1 except that volatile amine (trade name: MCC-H, product by Naigai Chemical Products Co., Ltd.) was introduced into the steam as an agent for corrosion prevention or corrosion inhibition for the metal pipe Pm so as to give a total amine concentration of 20 mg/L. The result thereof is shown in FIG. 7.

Comparative Example 4

Surface deterioration in test pieces was determined in the same manner as in Comparative Example 3 except that volatile amine (trade name: MCC-H, product by Naigai Chemical Products Co., Ltd.) was introduced into the steam as an agent for corrosion prevention or corrosion inhibition for the metal pipe Pm so as to give a total amine concentration of 20 mg/L. The result thereof is shown in Table 1.

TABLE 1

| | Anticorrosion agent or corrosion inhibitor | Surface deterioration | | |
| --- | --- | --- | --- | --- |
| | | Water phase region | Water line region | Vapor phase region |
| Comparative Example 2 | Absent | B | C | B |
| Comparative Example 4 | Present | A | A | A |

The result shown in FIG. 6 has revealed that the electric resistance value of the second testing member 22 (Example 1-2) for exclusively examining corrosion in the water line region is higher than the electric resistance values of the first testing member 21 (Example 1-1) for exclusively examining corrosion in the water phase region and the third testing member 23 (Example 1-3) for exclusively examining corrosion in the vapor phase region. That is, according to the result of Example 1, it has been determined that the metal pipe Pm has the severest corrosion in the water line region.

Meanwhile, according to the result of Comparative Example 2 shown in Table 1, it has been determined that the surface of the test piece exposed to the water line region had the severest deterioration. That is, the determination of the corrosion in Example 1 agrees with the determination in Comparative Example 2, and therefore it is considered that the determination in Example 1 correctly reflects the corrosion state in the actual environment in the metal pipe Pm.

Accordingly, an operator who has understood the result of Example 1 can take appropriate measures such as addition of an agent for preventing or inhibiting corrosion to the boiler steam and condensate system BS based on the result.

In contrast, the electric resistance value of the testing member of Comparative Example 1 for exclusively examining corrosion in the water phase region was much lower than the electric resistance value of the second testing member 22 of Example 1-2 for exclusively examining corrosion in the water line region. This indicates that not only does the determination in Comparative Example 1 fail to correctly reflect the corrosion state in the actual environment in the metal pipe Pm, but it may give an operator an incorrect understanding as if the corrosion state in the metal pipe Pm were better than it actually is. Consequently, the time of taking appropriate measures may be significantly delayed.

Furthermore, the result shown in FIG. 7 has revealed that the electric resistance changes in the conductive members 20a of Examples 2-1, 2-2 and 2-3 are substantially the same, and the electric resistance values thereof were lower than the electric resistance values of the conductive members 20a of Examples 1-1 and 1-3. That is, according to the result of Example 2, it has been determined that the corrosion progression was inhibited in all the regions (the water phase region, the water line region and the vapor phase region) in the metal pipe Pm.

Meanwhile, according to the result of Comparative Example 4 shown in Table 1, it has been determined that no surface deterioration was observed in all the regions (the water phase region, the water line region and the vapor phase region) in the test pieces. That is, the determination of the corrosion in Example 2 agrees with the determination in Comparative Example 4, and therefore it is considered that the determination in Example 2 correctly reflects the corrosion state in the actual environment in the metal pipe Pm.

In contrast, the electric resistance value of the testing member of Comparative Example 3 was much lower than the electric resistance values of the respective testing members 21 to 23 of Examples 2-1 to 2-3. This indicates that the determination in Comparative Example 3 may give an operator an incorrect understanding as if the corrosion state in the metal pipe Pm were much better than it actually is. Consequently, the operator may miss the time when the corrosion further progresses.

EXPLANATION OF REFERENCE NUMERALS

10 Steam introduction unit
11, 211 Container
11a Introduction port
12 Steam trap
13 Connection pipe
20 Corrosion testing unit
20a, 221 Conductive member
$20a_1$, 222 Reference Conductive member
20b, $20b_1$, 224, 225 Insulative Covering member
21-23 First to third testing members
21a Contact member in water line region
22a Contact member in water phase region
23a Contact member in vapor phase region
24 Reference resistance measuring member
30 Electric circuit unit
223a-223d First to fourth lead wires
B Boiler
BS Boiler steam and condensate system
M Agent feeding unit
Pb By-pass pipe
Pc Condensate pipe
Pm Metal pipe
Po Discharge pipe
Pw Water supply pipe
Rd Water line region
Rs Vapor phase region (steam region)
Rw Water phase region (condensed water region)
S Steam
T Water supply tank
$V_1$, $V_2$ Valve
W Condensed water
Wf Water surface
X Flow of steam

The invention claimed is:

1. A metal pipe corrosion monitoring device comprising:
a steam introduction unit for introducing thereinto steam flowing through a metal pipe; and
a corrosion testing unit provided in the steam introduction unit, characterized in that
the steam introduction unit is configured to generate condensed water by condensing some of the steam introduced thereinto to create a simulated environment similar to an actual environment in the metal pipe and discharge the condensed water above a predetermined water level to the outside, and
the corrosion testing unit has one or more contact members that contact with a water line region around a water surface of the condensed water in the steam introduction unit, a water phase region on a condensed water side with respect to the water line region and a vapor phase region on a steam side with respect to the water line region, and is configured to be able to measure an electric resistance of the one or more contact members.

2. The corrosion monitoring device according to claim 1, wherein the steam introduction unit has a steam trap on a side where the condensed water is discharged.

3. The corrosion monitoring device according to claim 1, wherein the steam introduction unit has a connection pipe to be connected to the metal pipe directly or via a by-pass pipe.

4. The corrosion monitoring device according to claim 3, wherein the steam introduction unit comprises a container for containing the corrosion testing unit, the container having an introduction port; and a holder being connected with the connection pipe and having a mounting recess in which the container is detachably fitted.

5. The corrosion monitoring device according to claim 1, wherein the corrosion testing unit comprises an electric circuit unit for detecting and displaying an electric resistance value of the one or more contact members.

6. The corrosion monitoring device according to claim 1, wherein the corrosion testing unit comprises a reference resistance measuring member having a conductive member covered with an insulative covering member so as not to be exposed in the steam introduction unit.

7. The corrosion monitoring device according to claim 1, wherein the corrosion testing unit has three separate contact members of which one contact member contacts only with the water phase region, another contact member contacts only with the water line region and the other contact member contacts only with the vapor phase region.

8. A contact member to be used in the corrosion monitoring device according to claim 7,
wherein the contact member contacts only with the water phase region, the water line region or the vapor phase region.

9. The contact member according to claim 8, comprising a bar-shaped conductive member.

10. The contact member according to claim 9,
wherein the conductive member is formed of the same material as the metal pipe.

11. The corrosion monitoring device according to claim 1, wherein the corrosion testing unit has one integrated contact member that contacts with the water phase region, the water line region and the vapor phase region.

12. A contact member to be used in the corrosion monitoring device according to claim 11,
wherein the contact member contacts with the water phase region, the water line region and the vapor phase region.

13. The contact member according to claim 12, comprising a thin-film-shaped conductive member.

14. Use of the corrosion monitoring device according to claim 1 in a system including the metal pipe through which steam flows, wherein the corrosion monitoring device is connected to the metal pipe to monitor corrosion of the metal pipe.

15. The use of the corrosion monitoring device according to claim 14, wherein the system is a boiler steam and condensate system.

* * * * *